US007858812B2

(12) United States Patent
Parthasaradhi Reddy et al.

(10) Patent No.: US 7,858,812 B2
(45) Date of Patent: Dec. 28, 2010

(54) PROCESS FOR ISOLATION OF DESIRED ISOMERS OF NEBIVOLOL INTERMEDIATES

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Itiyala Srinivas Reddy, Hyderabad (IN)

(73) Assignee: Hetero Drugs Limited (IN)

( * ) Notice: Subject to any disclaimer, the term of this patent is extended or adjusted under 35 U.S.C. 154(b) by 153 days.

(21) Appl. No.: 11/718,593

(22) PCT Filed: Jan. 18, 2006

(86) PCT No.: PCT/IN2006/000015

§ 371 (c)(1),
(2), (4) Date: May 3, 2007

(87) PCT Pub. No.: WO2007/083318

PCT Pub. Date: Jul. 26, 2007

(65) Prior Publication Data

US 2009/0076288 A1 Mar. 19, 2009

(51) Int. Cl.
*C07D 311/04* (2006.01)

(52) U.S. Cl. .................................................... 549/407

(58) Field of Classification Search .................. 549/407
See application file for complete search history.

(56) References Cited

U.S. PATENT DOCUMENTS 5,759,580 A 6/1998 Jans et al.

FOREIGN PATENT DOCUMENTS

| | | | |
|---|---|---|---|
| EP | 0145067 | A2 | 6/1985 |
| EP | 0334429 | A1 | 9/1989 |
| WO | WO 2006/016376 | A1 | 2/2006 |

OTHER PUBLICATIONS

H.Y. Aboul-Enein and I. Ali, HPLC Enantiomeric Resolution of Nebivolol on Normal and Reversed Amylose Based Chiral Phases, Pharmaceutical Analysis Laboratory, Biological and Medical Research Department, King Faisal Specialist Hospital and Research Centre, Riyadh, Saudi Arabia, (2001), 56(3), 214-216, Supplied by the British Library—The World's Knowledge.

PCT Notification of Transmittal of the International Search Report and the Written Opinion of the International Searching Authority, or the Declaration dated Jan. 18, 2006.

*Primary Examiner*—Bernard Dentz
(74) *Attorney, Agent, or Firm*—Caesar, Rivise, Bernstein, Cohen & Pokotilow, Ltd

(57) ABSTRACT

The present invention relates to a simple and commercially viable process for separation of desired isomers of nebivolol intermediates from a mixture containing undesired isomers of nebivolol intermediates. Thus, (+)-[2R*[1S*,5S*(S*)]]+[2R*[1S*,5R*(R*)]]-α,α'-[phenylmethyliminobis(methylene)]bis[6-fluoro-3,4-dihydro-2H-1-benzopyran-2-methanol] is dissolved in diisopropyl ether at reflux temperature and cooled to below about 30° C. to obtain the desired (+)-[2R*[1S*,5S*(S*)]]-α,α'-[phenylmethyliminobis(methylene)]bis[6-fluoro-3,4-dihydro-2H-1-benzopyran-2-methanol].

15 Claims, No Drawings

PROCESS FOR ISOLATION OF DESIRED ISOMERS OF NEBIVOLOL INTERMEDIATES

FIELD OF THE INVENTION

The present invention relates to a simple and commercially viable process for separation of desired isomers of nebivolol intermediates from a mixture containing undesired isomers of nebivolol intermediates.

BACKGROUND OF THE INVENTION

EP Patent No. 0145067 disclosed 2,2'-iminobisethanol derivatives. The compounds are antihypertensive agents. Among them nebivolol is racemic mixture of RSSS and its enantiomer of α,α'-[iminobis(methylene)]bis[6-fluoro-3,4-dihydro-2H-1-benzopyran-2-methanol] and the structures of these isomers are shown below with stereochemical notation at each chiral centre.

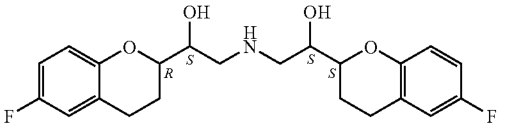

and

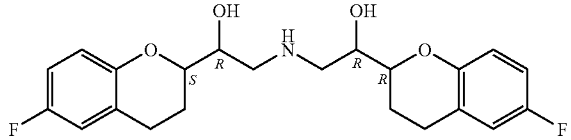

Processes for preparations of nebivolol and related compounds were described in EP Patent No. 0145067 and EP Patent No. 0334429. According to the processes described in these patents, chromatographic separations are required for the separation of diastereomeric pairs at the intermediate stage or at the final stage. The chromatographic separations involve additional operations, additional expensive setup adding to the cost of production. U.S. Pat. No. 5,759,580 described the separation of (±)-[2R*[1S*, 5S*(S*)]]-α,α'-[Iminobis(methylene)]bis[6-fluoro-3,4-dihydro-2H-1-benzopyran-2-methanol] hydrochloride (nebivolol hydrochloride) from the mixture of (±)-[2R*[1S*, 5S*(S*)]]±[2R*[1S*,5R*(R*)]]-α,α'-[iminobis(methylene)]bis[6-fluoro-3,4-dihydro-2H-1-benzopyran-2-methanol]. The yield of the nebivolol hydrochloride is extremely low (6.6%).

The PCT patent Application No. PCT/IN2004/000241 disclosed the isolation of racemic compound of formula A:

A

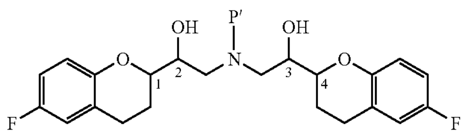

(±)-R*S*S*S* from the mixture of racemic compounds of formula B:

B

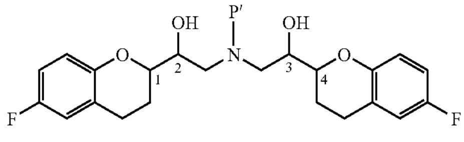

(±)-R*S*S*S*
+
(±)-R*S*R*R* wherein P' is a protecting group;

by converting the mixture of isomers into their hydrochloric acid salts, subjecting fractional crystallization of desired isomers as hydrochloride salts and neutralizing to obtain the corresponding free bases of desired isomers.

The racemic compounds of formula A are key intermediates having desired stereo chemistry in the preparation of nebivolol. These intermediates are subjected to deprotection to obtain nebivolol.

We have found that a process for separating the desired racemic compound of formula A from the mixture of a pair of racemic compounds represented by formula B by suspending or dissolving the mixture of a pair of racemic compounds of formula B in a suitable solvent and then isolating crystals to obtain the racemic compound of formula A.

The process of the present invention enables us to isolate desired isomers of nebivolol intermediates from the mixture containing undesired and desired isomers just by suspending or dissolving the mixture containing undesired and desired isomers in a suitable solvent and crystallizing without the need for the expensive chromatographic separations. The present invention also avoids the lengthy process for this separation of converting the mixture of isomers into their hydrochloride salts, fractional crystallization of desired isomers and converting back into desired isomers in free base form.

Moreover, the process of the invention may be repeated any number of times very easily just by suspending or dissolving in a suitable solvent and isolating until we get desired isomeric purity.

Thus, the present invention provides extremely simple and commercially viable process for isolating desired racemic compound from mixture of isomers also containing undesired isomers.

DETAILED DESCRIPTION OF THE INVENTION

The process for isolating racemic compound of formula I:

I

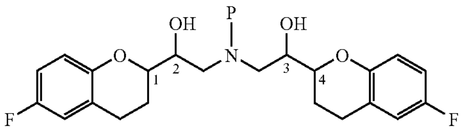

(±)-R*S*S*S* wherein

P is -allyl or 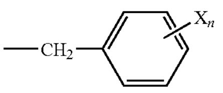

wherein X each independently is halo, nitro or $C_1$-$C_3$ alkyl and n is 0-5; from the mixture of racemic compounds of formula II:

II

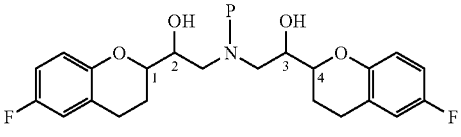

(±)-R*S*S*S*
+
(±)-R*S*R*R* wherein P is as defined in formula I;

the said process comprises suspending or dissolving the mixture of a pair of racemic compounds represented by formula II in an ether solvent and then isolating crystals to obtain the racemic compound of formula I.

Preferable ether solvent used is diisopropyl ether or diethyl ether and more preferable being diisopropyl ether.

The mixture of a pair of racemic compounds represented by formula II is dissolved in the ether solvent, preferably at 30° C. to reflux temperature of the solvent used, more preferably at 60° C. to reflux temperature of the solvent used and still more preferably at reflux temperature of the solvent used, and precipitated the compound of formula I.

The precipitation of the racemic compound of formula I may be carried out by cooling, seeding, partial removal of the solvent from the solution, by adding an anti-solvent to the solution or a combination thereof. Preferably the precipitation of the racemic compound of formula I is carried out by cooling.

The more preferred compound of formula I prepared according to the present invention is the compound of formula Ia:

Ia

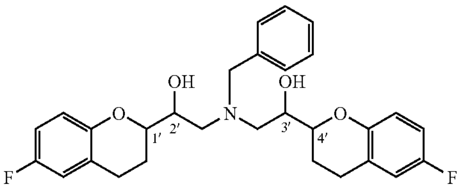

(±)-R*S*S*S*

A preferable process of the invention is described below:

The mixture of a pair of racemic compounds represented by formula II is dissolved in diisopropyl ether at 30° C. to reflux temperature and cooled to obtain desired racemic compound of formula I as crystalline product. A more preferable process of the invention is described below:

The mixture of a pair of racemic compounds represented by formula II, wherein P is benzyl, is dissolved in diisopropyl ether at reflux temperature and cooled to below 30° C., more preferably between 15-30° C. to obtain the desired racemic compound of formula I, wherein P is benzyl.

As another preferable process, a suspension of the mixture of a pair of racemic compounds represented by formula II in diisopropyl ether is stirred for at least 30 minutes at 10° C. to reflux temperature of the solvent used, more preferably for 1 hour to 4 hours at below 60° C. and still more preferably for 1 hour to 3 hours at 10-40° C. and isolating the desired racemic compound of formula I by known methods such as filtration or centrifugation.

Stereochemical description describing the configurations at chiral centers used here is in the order (1,2,3 and 4) mentioned in the structure. Thus, for example, the stereochemical description R*S*S*S* shown in the formula I refers to R* configuration at the carbon ‘1’, S* configuration at 2 and so on and R*S*S*S* has the meaning shown below:

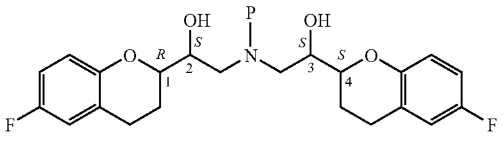

RSSS

+

-continued

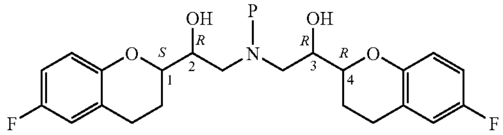

SRRR

The stereochemical description R*S*R*R* used in the formula II has the meaning shown below:

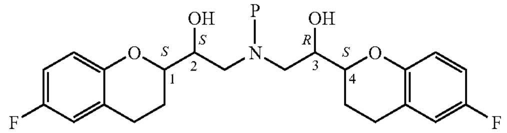

SSRS

+

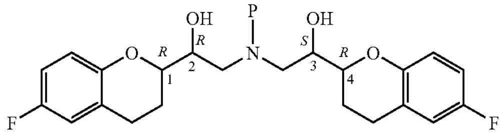

RRSR

The process can be repeated until the separation of the desired racemic compound is obtained in desired isomeric purity.

The racemic compounds of formula I are intermediates for preparing nebivolol by removing the protecting group ‘P’ by the processes known in the art and optionally converting nebivolol into a pharmaceutically acceptable salt.

The desired racemic compound of formula I may further be debenzylated by known methods to obtain nebivolol of formula III:

III

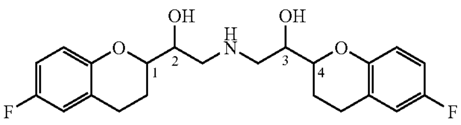

(±)-R*S*S*S*

The invention will now be further described by the following examples, which are illustrative rather than limiting.

EXAMPLE 1

The solution of benzyl amine (120 gm) in ethanol (730 ml) was added to a mixture of (±)-[S*(R*)]-6-fluoro-3,4-dihydro-2-oxiranyl-2H-1-benzopyran (73 gm) and ethanol (730 ml) drop wise at reflux temperature for 15 minutes. The temperature of the reaction mixture was raised to reflux and maintained for 5 hours at reflux temperature. Then ethanol was distilled off under vacuum at 50° C. To this residue diisopropyl ether (400 ml) was added and stirred for 30 minutes at 0-5° C. Then the separated solid was filtered, washed with chilled diisopropylether and dried to give 69 gm of (±)-[1S*(R*)]-6-fluoro-3,4-dihydro-α-[[(phenylmethyl)amino]methyl]-2H-1-benzopyran-2-methanol (HPLC purity: 97%).

EXAMPLE 2

The mixture of (±)-[1S*(S*)]-6-fluoro-3,4-dihydro-2-oxiranyl-2H-1-benzopyran (65 gm) and ethanol (1400 ml) was stirred for 10 minutes, (±)-[1S*(R*)]-6-fluoro-3,4-dihydro-α-[[(phenylmethyl)amino]methyl]-2H-1-benzopyran-2-methanol (69 gm, obtained in example 1) was added and stirred for 10 minutes. The contents were heated to reflux and stirred for 26 hours at the same temperature to obtain (±)-[2R*[1S*,5S*(S*)]]±[2R*[1S*,5R*(R*)]]-α,α'-[phenylmethyliminobis(methyl ene)]bis[6-fluoro-3,4-dihydro-2H-1-benzopyran-2-methanol] ((±)-[2R*[1S*,5S* (S*)]] to (±)-[2R*[1S*,5R*(R*)]] ratio was 0.83:1.0). Then the reaction mass was cooled to 40-50° C., distilled off the solvent completely under reduced pressure until the mass temperature reaches 50-55° C. and then co-distilled twice with diisopropyl ether (each time 65 ml) under reduced pressure until the mass temperature reaches 50-55° C. To the residue, diisopropyl ether (580 ml) was added, heated to reflux and refluxed for 1 hour 30 minutes. The reaction mass was cooled to 25-35° C., stirred for 4 hours, filtered the material and washed with diisopropyl ether (85 ml). The resulting wet cake was added to diisopropyl ether (420 ml), heated to reflux and then stirred for 1 hour. The resulting mass was cooled to 25-35° C. and stirred for 4 hours at 25-35° C. Filtered the solid, washed with 40 ml of diisopropyl ether and dried at 45-55° C. to give 48 gm of (±)-[2R*[1S*,5S*(S*)]]-α,α'-[phenylmethyliminobis(methylene)]bis[6-fluoro-3,4-dihydro-2H-1-benzopyran-2-methanol] (HPLC purity 99.1%; (±)-[2R*[1S*, 5S*(S*)]] to (±)-[2R*[1S*,5R*(R*)]] ratio is 98:1).

EXAMPLE 3

The mixture of (±)-[2R*[1S*,5S*(S*)]]-α,α'-[phenylmethyliminobis (methylene)]bis[6-fluoro-3,4-dihydro-2H-1-benzopyran-2-methanol] (48 gm), acetic acid (480 gm) and 5% palladium on charcoal (19 gm) was taken into a hydrogenation flask and subjected to hydrogenation under a hydrogen gas pressure of 1.5 kg/$cm^2$ for 3 hours at 25-40° C. Then the reaction mixture was filtered on hi-flo and washed with acetic acid (55 gm). The solvent was distilled off completely under reduced pressure and then co-distilled twice with ethyl acetate (each time 60 ml). To the resulting mass, ethyl acetate (480 ml) was added, refluxed for 1 hour and then cooled to 25-35° C. The reaction mass was stirred for 4 hours, again cooled to 0-10° C. and stirred for 1 hour 30 minutes. Filtered the material and washed with ethyl acetate (60 ml). The resulting wet cake was stirred with methanol (850 ml) and 25% monomethyl amine (60 ml) for 1 hour at 25-35° C., cooled to 0-10° C. and then stirred for 1 hour at 0-10° C. Filtered the material and washed with methanol (60 ml) to give 40.5 gm of (±)-[2R*[1S*,5S*(S*)]]-α,α'-[iminobis(methylene)]bis[6-fluoro-3,4-dihydro-2H-1-benzopyran-2-methanol] (Nebivolol) (HPLC purity: 99.2%).

EXAMPLE 4

The mixture of nebivolol (48.5 gm) and methanol (950 ml) was refluxed for 30 minutes and then subjected to carbon treatment. The resulting mass was cooled to 0-10° C., hydrochloric acid (6.5 ml) was slowly added during 30 minutes and then stirred for 4 hours at 0-10C. Filtered the material, washed with 50 ml of methanol and dried at 50-60° C. to give 27.5 gm of Nebivolol hydrochloride salt (HPLC purity: 99.5%).

We claim:

1. A process for isolating the racemic compound of formula I:

I

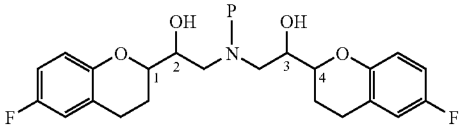

(±)-R*S*S*S* wherein

P is -allyl or 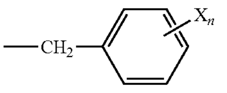

wherein X each independently is halo, nitro or $C_1$-$C_3$ alkyl and n is 0-5;

from the mixture of racemic compounds of the formula II:

II

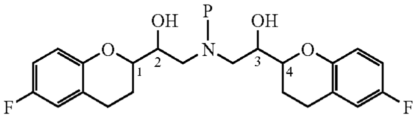

(±)-R*S*S*S*
+
(±)-R*S*R*R* wherein P is as defined in formula I;

the process comprising, suspending or dissolving the mixture of a pair of racemic compounds represented by formula II in an ether solvent and then isolating crystals to obtain the racemic compound of formula I.

2. The process as claimed in claim 1, wherein the ether solvent used is diisopropyl ether or diethyl ether.

3. The process as claimed in claim 2, wherein the ether solvent is diisopropyl ether.

4. The process as claimed in claim 1, wherein the mixture of a pair of racemic compounds represented by formula II is dissolved in the ether solvent at about 30° C. to reflux temperature of the solvent used and the compound of foimula I is precipitated.

5. The process as claimed in claim 4, wherein the compound of formula II is dissolved in the ether solvent at about 60° C. to reflux temperature of the solvent used.

6. The process as claimed in claim 4, wherein the precipitation of the racemic compound of formula I is carried out by cooling, seeding, partial removal of the solvent from the solution, by adding an anti-solvent to the solution or a combination thereof.

7. The process as claimed in claim 6, wherein the precipitation is carried out by cooling.

8. The process as claimed in claim 1, wherein the mixture of a pair of racemic compounds represented by formula II is dissolved in diisopropyl ether at the reflux temperature of the solvent used and the compound of formula I is precipitated by cooling to below about 30° C.

9. The process as claimed in claim 8, wherein the compound of formula II, wherein P is benzyl, is dissolved in diisopropyl ether at its reflux temperature and cooled to below 30° C. to obtain the desired racemic compound of formula I, wherein P is benzyl.

10. The process as claimed in claim 1, wherein the suspension of the mixture of a pair of racemic compounds represented by formula II in diisopropyl ether is stirred for at least 30 minutes at about 10° C. to the reflux temperature of the solvent used and then the desired racemic compound of formula I is isolated.

11. The process as claimed in claim 10, wherein the suspension is stirred for 1 hour to 4 hours at below about 60° C.

12. The process as claimed in claim 11, wherein the suspension is stirred for 1 hour to 3 hours at about 10 -40° C.

13. The process as claimed in claim 10, wherein the isolation of the racemic compound of formula I is carried out by filtration or centrifugation.

14. The process as claimed in claim 1, wherein the racemic compound of formula I prepared according to the present invention is the compound of formula Ia:
Ia
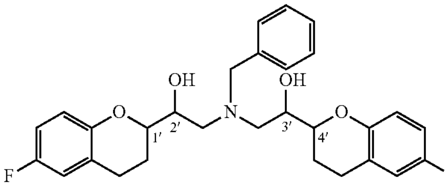
(±)-R*S*S*S*.
15. The process as claimed in claim 1, wherein the desired racemic compound of formula I is further debenzylated by known methods to obtain nebivolol of formula III:
III
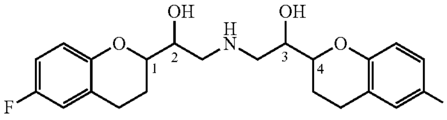
(±)-R*S*S*S*.
* * * * *